(12) United States Patent
Ramadoss et al.

(10) Patent No.: US 8,617,108 B2
(45) Date of Patent: Dec. 31, 2013

(54) LIFTER ASSEMBLY

(75) Inventors: Mohanlal Ramadoss, Hong Kong (CN); Wai To Li, Hong Kong (CN); Yue Fu Zhu, Shenzhen (CN); Xiang Dong Jiang, Shenzhen (CN)

(73) Assignee: Johnson Electric S.A., Murten (CH)

( * ) Notice: Subject to any disclaimer, the term of this patent is extended or adjusted under 35 U.S.C. 154(b) by 493 days.

(21) Appl. No.: 12/847,620

(22) Filed: Jul. 30, 2010

(65) Prior Publication Data

US 2011/0023644 A1 Feb. 3, 2011

(30) Foreign Application Priority Data

Jul. 30, 2009 (CN) .......................... 2009 1 0109184

(51) Int. Cl.
*A61M 37/00* (2006.01)

(52) U.S. Cl.
USPC ........... 604/131; 604/136; 604/152; 604/154; 604/155; 604/201

(58) Field of Classification Search
USPC .................. 604/131, 136, 152, 154, 155, 201
See application file for complete search history.

(56) References Cited

U.S. PATENT DOCUMENTS

| | | | | |
|---|---|---|---|---|
| 1,966,498 A | * | 7/1934 | Gross | 417/519 |
| 3,185,153 A | * | 5/1965 | Leucci | 604/31 |
| 3,327,994 A | * | 6/1967 | Carl | 251/368 |
| 3,820,545 A | * | 6/1974 | Jefferts | 606/117 |
| 4,398,327 A | * | 8/1983 | Yamazaki | 29/33 R |
| 4,672,967 A | * | 6/1987 | Smith | 606/117 |
| 4,787,893 A | * | 11/1988 | Villette | 604/188 |
| 4,846,797 A | * | 7/1989 | Howson et al. | 604/154 |
| 5,002,546 A | * | 3/1991 | Romano | 606/80 |
| 5,055,109 A | * | 10/1991 | Gould et al. | 604/95.01 |
| 5,279,552 A | * | 1/1994 | Magnet | 604/47 |
| 5,484,414 A | * | 1/1996 | Pace | 604/110 |
| 5,505,697 A | * | 4/1996 | McKinnon et al. | 604/71 |
| 5,558,639 A | * | 9/1996 | Gangemi et al. | 604/67 |
| 5,578,014 A | * | 11/1996 | Erez et al. | 604/192 |
| 5,927,976 A | * | 7/1999 | Wu | 433/82 |
| 5,928,201 A | * | 7/1999 | Poulsen et al. | 604/208 |
| 5,957,896 A | * | 9/1999 | Bendek et al. | 604/207 |
| 5,971,963 A | * | 10/1999 | Choi | 604/177 |
| 5,980,545 A | * | 11/1999 | Pacala et al. | 606/170 |
| 6,003,736 A | | 12/1999 | Ljunggren | |
| 6,508,788 B2 | | 1/2003 | Preuthun | |
| 6,969,370 B2 | | 11/2005 | Langley et al. | |
| 7,001,360 B2 | | 2/2006 | Veasey et al. | |

(Continued)

FOREIGN PATENT DOCUMENTS

| | | | | |
|---|---|---|---|---|
| JP | 10225065 A | * | 8/1998 | H02K 11/00 |
| WO | WO2008/142394 A1 | | 11/2008 | |

*Primary Examiner* — Nicholas Lucchesi
*Assistant Examiner* — Scott Medway
(74) *Attorney, Agent, or Firm* — Muncy, Geissler, Olds & Lowe, PLLC (57) ABSTRACT

A lifter assembly for actuating a needle of an automatic medication delivery device, includes a motor, a speed reduction device driven by the motor, an output shaft driven by the speed reduction device via a rigid transmission device, a driving lever configured to move the needle, the driving lever being connected to and driven by the output shaft, and a sensing device configured to sense the rotation position of the output shaft. The speed reduction device comprises a worm in mesh with a worm gear. The output shaft, the worm gear and the rigid transmission device cooperatively constitute a four-bar linkage mechanism.

12 Claims, 5 Drawing Sheets

(56) References Cited

U.S. PATENT DOCUMENTS

| | | | |
|---|---|---|---|
| 7,025,226 B2 | 4/2006 | Ramey | |
| 7,442,186 B2 | 10/2008 | Blomquist | |
| 7,516,873 B2 * | 4/2009 | Wang | 222/333 |
| 7,534,226 B2 * | 5/2009 | Mernoe et al. | 604/155 |
| 7,670,328 B2 * | 3/2010 | Miller | 604/506 |
| 7,794,426 B2 * | 9/2010 | Briones et al. | 604/131 |
| 7,981,102 B2 * | 7/2011 | Patel et al. | 604/500 |
| 8,057,434 B2 * | 11/2011 | Burroughs et al. | 604/131 |
| 8,057,436 B2 * | 11/2011 | Causey et al. | 604/151 |
| 2004/0186432 A1 * | 9/2004 | Barry et al. | 604/152 |
| 2005/0154410 A1 * | 7/2005 | Conway et al. | 606/181 |
| 2005/0177111 A1 | 8/2005 | Ozeri | |
| 2005/0234494 A1 * | 10/2005 | Conway et al. | 606/181 |
| 2005/0245956 A1 | 11/2005 | Steinemann et al. | |
| 2006/0184124 A1 * | 8/2006 | Cowan et al. | 604/155 |
| 2007/0233001 A1 | 10/2007 | Burroughs et al. | |
| 2008/0097381 A1 * | 4/2008 | Moberg et al. | 604/506 |
| 2009/0227958 A1 | 9/2009 | Burroughs et al. | |
| 2010/0152660 A1 | 6/2010 | Mack et al. | |

* cited by examiner

LIFTER ASSEMBLY

CROSS REFERENCE TO RELATED APPLICATIONS

This non-provisional patent application claims priority under 35 U.S.C. §119(a) from Patent Application No. 200910109184.4 filed in The People's Republic of China on Jul. 30, 2009.

FIELD OF THE INVENTION

This invention relates to a lifter assembly for an automatic medication delivery device.

BACKGROUND OF THE INVENTION

US patent application No. 20070233001 discloses an injection apparatus for delivering a pharmaceutical liquid to a patient. The injection apparatus comprises a needle cassette containing a plurality of drug injection needles; a drug cartridge containing a liquid and including a sealable aperture for accessing the liquid, a drive assembly engageable with the drug cartridge to expel the liquid through the aperture; a lifter assembly engageable with the needle cassette to drive one of the needles into a patient while simultaneously accessing the liquid in the drug cartridge through the aperture and thereafter to withdraw the needle from the patient after a measured dose of the liquid has been administered. The lifter assembly uses two springs. One spring acts to move the lifter downward to drive the needle into the patient at the start of an injection. The other spring acts to move the lifter upward to thereby withdraw the needle from the patient after a medicine injection is completed.

However, it is difficult to stably and precisely control movement of the needles using a lifter assembly which uses springs to drive the needles.

Hence there is a desire for an improved lifter assembly which can overcome the above mentioned problem.

SUMMARY OF THE INVENTION

Accordingly, in one aspect thereof, the present invention provides a lifter assembly for actuating a needle of an automatic medication delivery device. The lifter assembly comprises: a motor having a motor shaft; a speed reduction device driven by the motor; an output shaft driven by the speed reduction device via a rigid transmission device; a driving lever configured to move the needle, the driving lever being connected to and driven by the output shaft; and a sensing device configured to sense the rotational position of the output shaft.

Preferably, the speed reduction device comprises a worm and a worm gear in mesh with the worm; with the output shaft, the worm gear and the rigid transmission device cooperatively constituting a four-bar linkage mechanism.

Preferably, the worm gear comprises a connection structure offset from the center of the worm gear; the rigid transmission device comprises an arm having one end fixed to the output shaft and the other end extending away from the output shaft, and a linkage lever having two opposite ends respectively pivotably attached to the other end of the arm and to the connection structure of the worm gear; and the center of the worm gear, the joints between the linkage lever and the worm gear and the arm, and the center of the output shaft constituting four points of the four-bar linkage mechanism.

Preferably, the joints between the linkage lever and the worm gear and the arm are formed by a post on one part being pivotably received in a corresponding hole in the other part of the respective joint.

Preferably, the lifter assembly has a housing fastened to the motor, and the four-bar linkage mechanism is disposed within the housing.

Preferably, a limit structure is arranged between the housing and the output shaft to preventing the output shaft from rotating beyond a predetermined range.

Preferably, the limit structure comprises a limit block formed on the housing, and a pair of projections extending from the output shaft and being arranged to abut against the limit block when the output shaft rotates to the end of the predetermined range in a clockwise direction and an anticlockwise direction, respectively.

Preferably, the sensing device comprises an encoder disc fixed to and rotatable with the output shaft, and a sensor adjacent to and cooperating with the encoder disc.

Preferably, a circuit board is fastened to the housing, the sensor is disposed on one side of the circuit board and an electrical connector is disposed on an opposite side of the circuit board and exposed to outside of the housing.

Preferably, the driving lever is connected to the output shaft via a connecting member which is formed as a monolithic construction with one of the output shaft and the driving lever and is attached to the other of the output shaft and the driving lever.

Alternatively, the driving lever is connected to the output shaft via a connecting member, the connecting member having an end with a non-circular configuration matched with a non-circular hole in the output shaft, and an opposite end fixedly received in a hole in the driving lever.

Preferably, the worm is fixed to the motor shaft whereby the motor drives the worm gear via the worm.

Preferably, the housing comprises a seat, the worm gear is pivotably attached to the seat, the axis of the worm gear is parallel to the axis of the output shaft and perpendicular to the motor shaft.

BRIEF DESCRIPTION OF THE DRAWINGS

A preferred embodiment of the invention will now be described, by way of example only, with reference to figures of the accompanying drawings. In the figures, identical structures, elements or parts that appear in more than one figure are generally labeled with a same reference numeral in all the figures in which they appear. Dimensions of components and features shown in the figures are generally chosen for convenience and clarity of presentation and are not necessarily shown to scale. The figures are listed below.

DETAILED DESCRIPTION OF THE PREFERRED EMBODIMENTS

Figure 1:
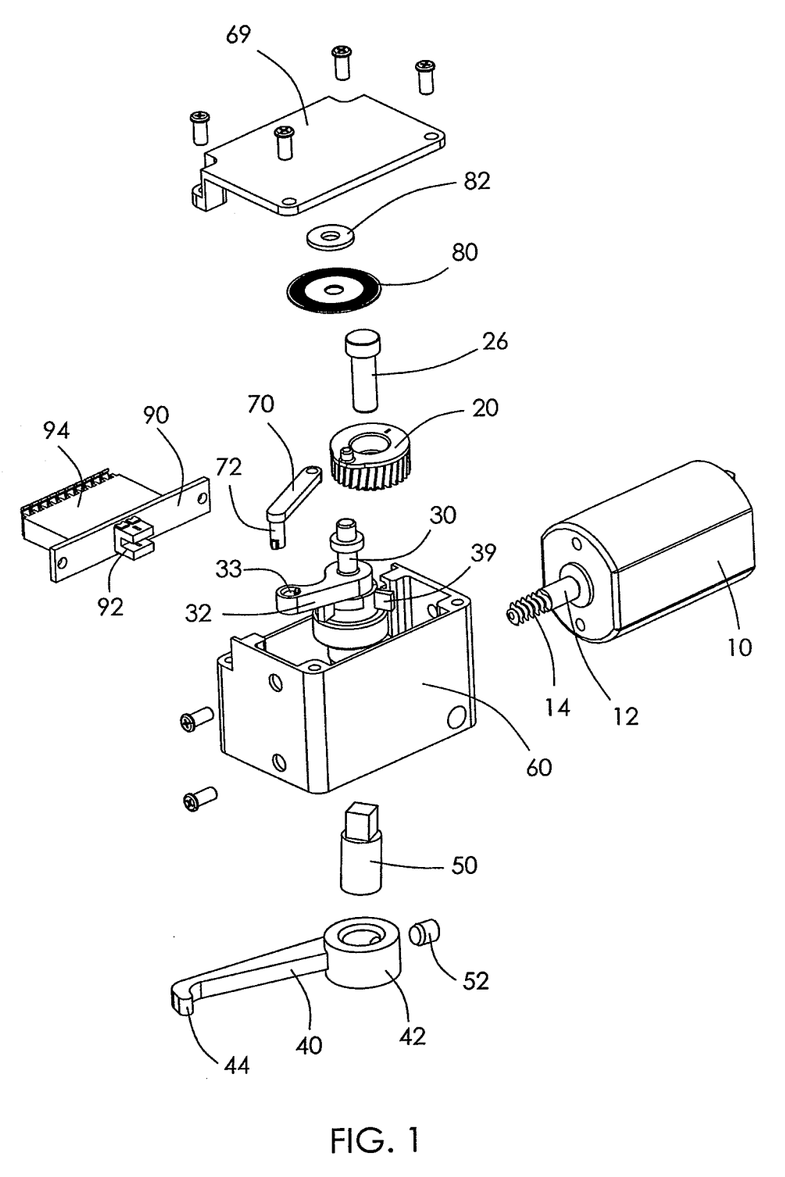
FIG. 1 is an exploded view of a lifter assembly in accordance with one embodiment of the present invention.

Referring to FIG. 1, the motor 10 has a motor shaft 12. The speed reduction device comprises a worm 14 arranged at the motor shaft 12 and a worm gear 20 meshed with the worm 14. The driving lever 40 is connected to one end of the output shaft 30 via a connecting member 50. The lifter assembly further comprises a housing 60 for accommodating the speed reduction device and the output shaft 30. The housing 60 is fastened with the housing of the motor 10 via screws (not labeled).

Figure 2:
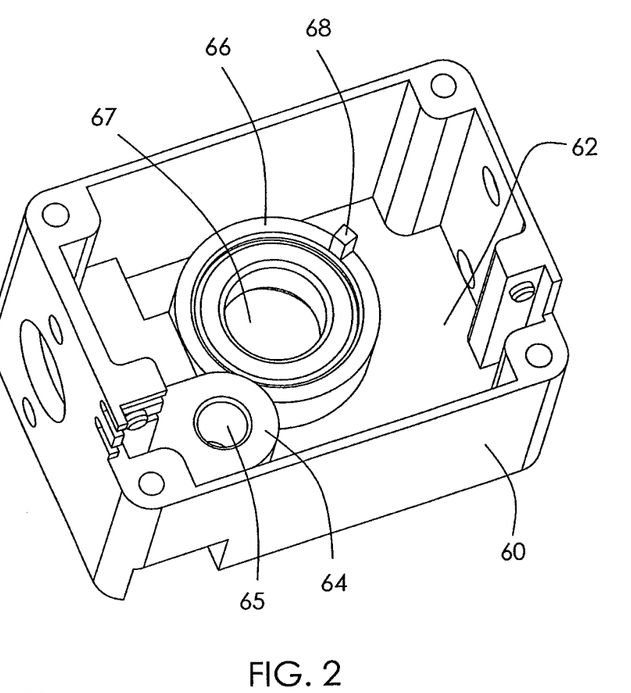
FIG. 2 is an isometric view of a housing of the lifter assembly of FIG. 1.

Referring to FIG. 2, the housing 60 comprises a bottom plate 62 on which a seat 64 is provided. The seat 64 defines a mounting hole 65. A cylindrical mount 66 is arranged at a middle of the bottom plate 62. The mount 66 defines a stepped through hole 67. A limit block 68 is formed on the end surface of the mount 66 away from the bottom plate 62.

Figure 3:
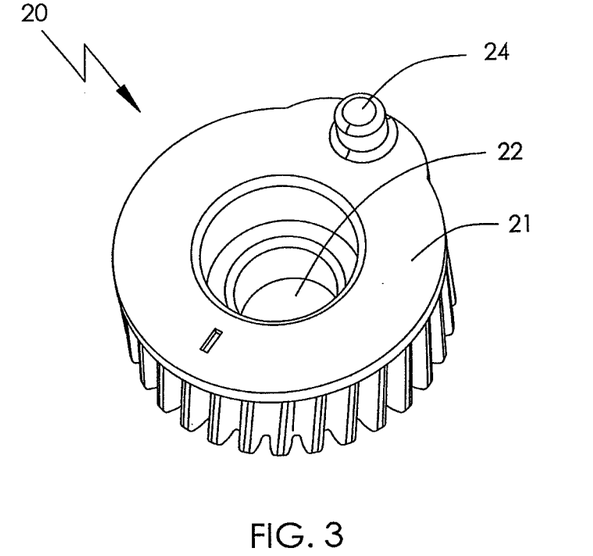
FIG. 3 is an isometric view of a worm of the lifter assembly of FIG. 1.

Referring to FIG. 3, the worm gear 20 has a stepped through hole 22 at the center thereof. A connection structure, optionally in the form of a post 24 as shown, extends axially from a point of the end surface 21 of the worm gear 20 offset from the center of the worm gear 20. Alternatively, the connection structure could be a hole.

Referring to FIGS. 4 to 8, the worm gear 20 is pivotably attached to the seat 64 via a pin 26 which extends through the through hole 22 of the worm gear 20 and is press fitted into the mounting hole 65 of the seat 64. The pin 26 has an enlarged head which is received in the larger portion of the stepped through hole 22 of the worm gear 20 and abuts against the shoulder of the stepped through hole 22 to capture the worm gear to the pin 26. Preferably, the top surface of the head of the pin 26 is coplanar with the end surface 21 of the worm gear 20. The worm gear 20 is pivotable about the pin 26 which is fixed with the seat 64 of the housing 60. The axis of the worm gear 20 is parallel to the axis of the output shaft 30 and perpendicular to the motor shaft 12 of the motor 10. The end 34 of the output shaft 20 is pivotably attached to the stepped through hole 67 via a bearing 36 which is fixedly received in the larger portion of the stepped through hole 67. The end 34 extends through the through hole 67 to outside of the housing 60 (shown in FIG. 6).

Figure 4:
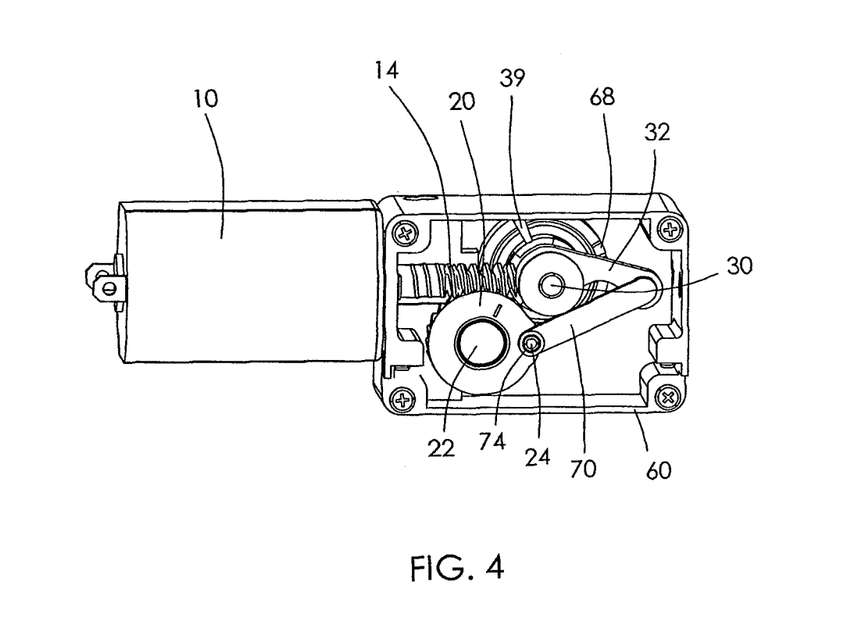
FIG. 4 is a partially assembled plan view of the lifter assembly of FIG. 1 with a top plate of the housing and a position sensor removed to show components within the housing.

Referring to FIG. 1 and FIG. 4, an arm 32 has one end fixed with the output shaft 30 and the other end extending away from the output shaft 30. A pivot hole 33 is defined at the other end of the arm 32. A linkage lever 70 is pivotably connected between the worm gear 20 and the arm 32. The linkage lever 70 has a post 72 extending from one end thereof, and a pivot hole 74 formed in the other end thereof. The post 72 of the linkage lever 70 is pivotably received in the pivot hole 33 of the arm 32. The post 24 of the worm gear 20 is pivotably received in the pivot hole 74 of the linkage lever 70. Understandably, the position of the pivot holes 33 and 74 and the position of the posts 72 and 24 are interchangeable. The posts 72,24 may be integrally formed with the linkage lever 70, worm gear 20, or fastened to the linkage lever 70, worm gear 20 after being formed.

Figure 5:
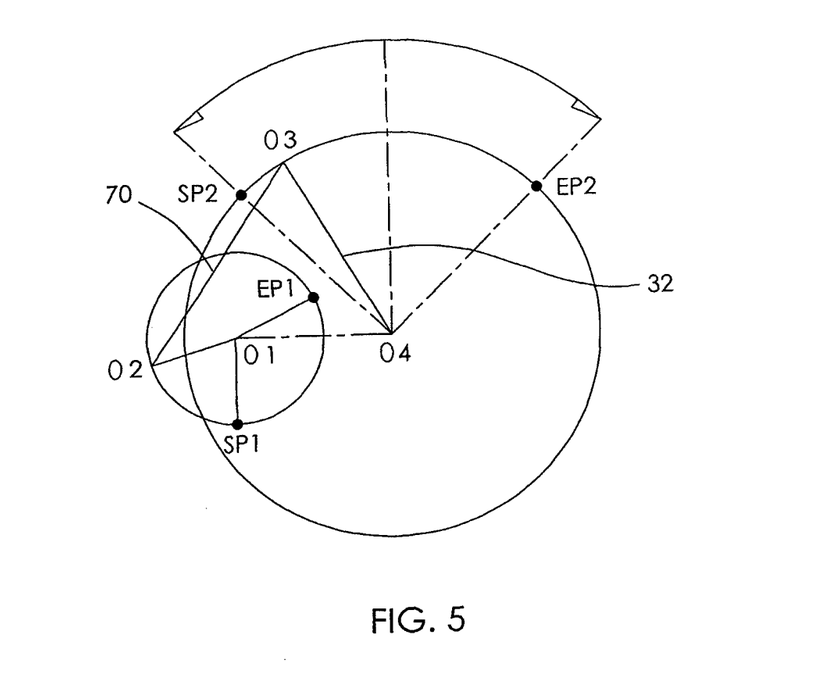
FIG. 5 is a schematic diagram of a four-bar linkage mechanism of the lifter assembly of FIG. 1.
Figure 6:
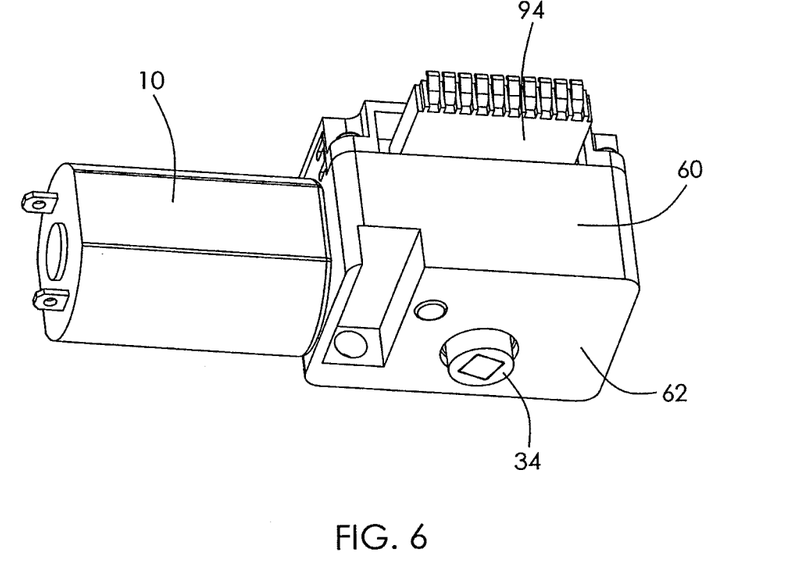
FIG. 6 is an isometric view from one side and below of the lifter assembly of FIG. 1 with a driving lever removed.

As shown schematically in FIG. 5, the worm gear 20, linkage lever 70, arm 32 and output shaft 30 cooperatively form a rigid four-bar linkage mechanism. The line from the center O1 of the worm gear 20 to the center O2 of the post 24 of the worm gear 20 constitutes a first bar of the four-bar linkage mechanism. The linkage lever 70 constitutes a second bar of the four-bar linkage mechanism. The arm 32 constitutes a third bar which extends from the joint O3 between the linkage lever 70 and the arm 32 to the center O4 of the output shaft 30. The line from the center O4 of the output shaft 30 to the center O1 of the worm gear 20 constitutes a fourth bar of the four-bar linkage mechanism. When the motor 10 rotates the worm gear 20 in a clockwise direction the center O2 of the post 24 moves from the start point SP1 to the end point EP1 in the clockwise direction, the arm 32 is driven to rotate by the linkage lever 70 and the joint O3 between the linkage lever 70 and the arm 32 is moved from the start point SP2 to the end point EP2 in a clockwise direction. The degree of rotation of the arm 32 is less than that of the worm gear 20. That means, the output shaft 30 rotates slower than the worm gear 20. When the motor 10 rotates the worm gear 20 in an anti-clockwise direction to return the center O2 of the post 24 from the end point EP1 to the start point SP1 in the anti-clockwise direction, the arm 32 is driven by the linkage lever 70, and the joint O3 between the linkage lever 70 and the arm 32 is moved from the end point EP2 to the start point SP2 in the anti-clockwise direction. A pair of projections 39 extends from the periphery of the output shaft 30 for coacting with the limit block 68 of the housing 60 to keep rotation of the output shaft 30 within a predetermined range. When the joint O3 between the linkage lever 70 and the arm 32 arrives at the start point SP2 or end point EP2, a corresponding one of the projections 39 will abut against the limit block 68 of the housing 60 to stop the output shaft 30 from rotating further.

Alternatively, the motor 10 may be arranged to only drive the worm gear 20 in a single direction such as to rotate only in the clockwise direction to cause the center O2 of the post 24 to return from the end point EP1 to the start point SP1 in the clockwise direction, to thereby return the arm 32 to its original position in the clockwise direction. In the return path where the motor 10 continues to rotate in the same direction, the output shaft 30 rotates quicker than the worm gear 20. This arrangement may be preferred if faster withdrawal of the needle from the patient is desired.

Figure 7:
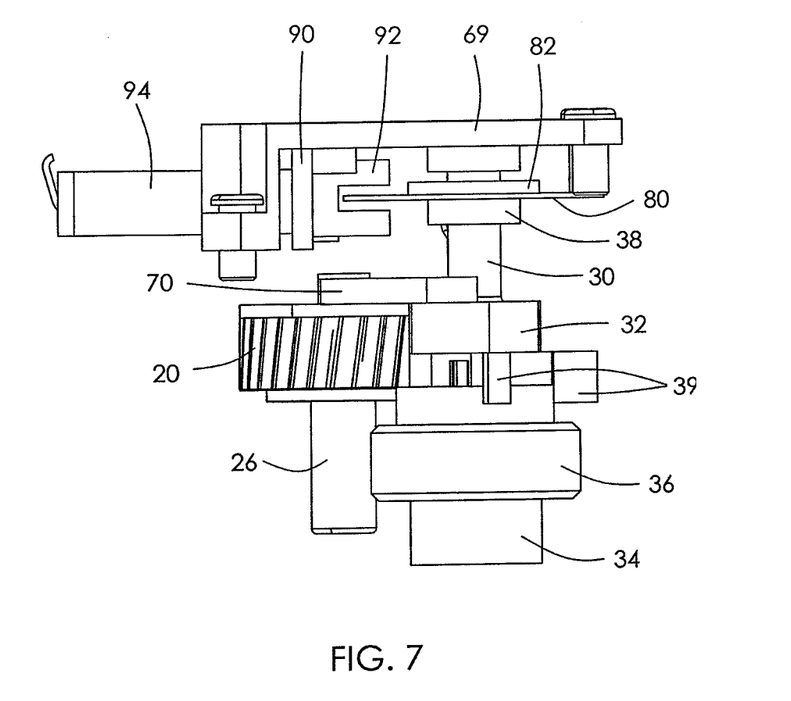
FIG. 7 is an end view of the lifter assembly of FIG. 6 with the motor and parts of the housing removed.
Figure 8:
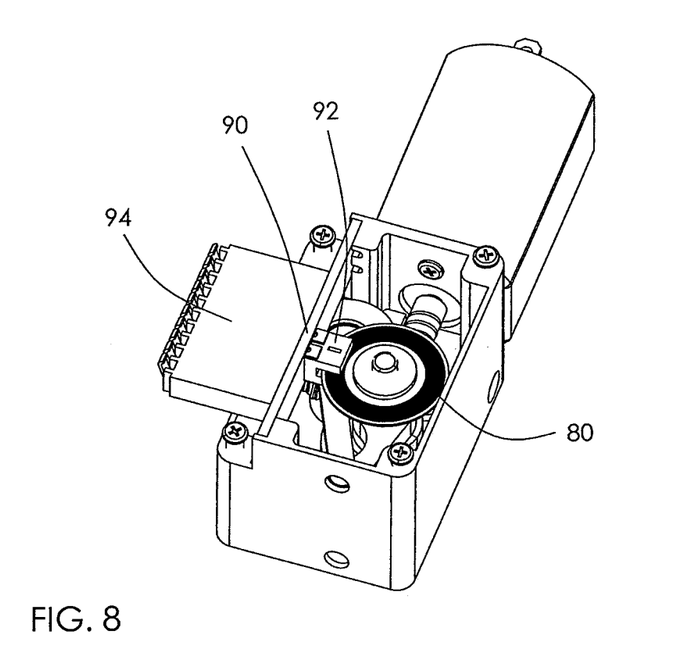
FIG. 8 is an isometric view from one end and above of the lifter assembly of FIG. 1 with a top cover removed similar to show the position sensor.

Referring to FIGS. 7 and 8, an annular shoulder 38 is formed at the other end of the output shaft 30. An encoder disc 80 is supported on the shoulder 38 and fixed to the shoulder 38 by a mounting washer 82. The mounting washer 82 has a mounting hole into which the output shaft 30 is press fitted. The disc 80 is sandwiched between the shoulder 38 and the mounting washer 82 and is thus fixed to and rotated with the output shaft 30. The end of the output shaft 30 extends through the encoder disc 80 and the mounting washer 82 to be pivotably attached to the top plate 69. A circuit board 90 is attached to one side of the housing 60. A sensor 92 is arranged on one side of the circuit board 90 facing the disc 80, for sensing the rotational position of the disc 80. An electrical connector 94 is arranged on the other side of the circuit board 90 and exposed to the outside of the housing 60 for connecting with a power source and/or the control center of the medication delivery device. The circuit board 90 is communicated with the control center such that signals generated by the sensor 92 may be sent to the control center.

Figure 9:
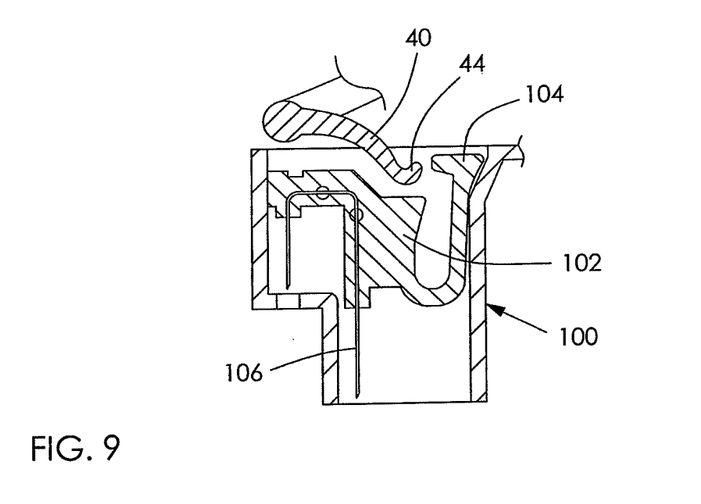
FIG. 9 shows a hook of the driving lever and a part of a needle cassette.

Referring to FIG. 1 again, the connecting member 50 is optionally formed separately from the driving lever 40. One end of the connecting member 50 has a rectangular shape for being fittingly received in the rectangular hole 35 (shown in FIG. 6) of the output shaft 30. The other end of the connecting member 50 has a round shape for being received in the round hole 42 of the driving lever 40 and being fixed in the hole 42 via a pin or grub screw 52 which is inserted radially through the wall of the hole 42 to engage the connecting member 50. The driving lever 40 is thus rotatable with the output shaft 30. Alternatively, the connecting member 50 may be integrally formed with the driving lever 40 or the output shaft 30 as schematically illustrated in FIG. 9. The distal end of the driving lever 40 forms a hook 44.

Referring also to FIG. 9, in operation, the motor 10 drives the worm gear 20 via the worm 14 to rotate in a direction, for example in a clockwise direction. The worm gear 20 drives the output shaft 30 to rotate in the clockwise direction via the linkage lever 70 and the arm 32. The output shaft 30 drives the driving lever 40 to rotate about the axis of the hole 42 in the clockwise direction. The hook 44 formed at the distal end of the driving lever 40 moves towards and engages a needle support of the needle cassette 100 of the medication delivery device. The motor continues to drive the arm 32 until the control center of the medication delivery device detects that the disc 80 has rotated through a predetermined angle, and sends a stop signal to the motor 10 to thereby stop the motor 10. As the arm presses the needle carrier 102, the hook 44 of the driving lever 40 slips down to below the barb 104 of the needle support 102 and pushes the needle support 102 downward to cause one end of the needle 106 out of the cassette and to insert into a patient and the other end to communicate with a drug cartridge of the medication delivery device to thereby allow a pharmaceutical liquid drug to be delivered to the patient. After the pharmaceutical liquid drug has been delivered to the patient, the control center controls the motor 10 to rotate in a reverse direction, for example in an anti-clockwise direction, to thereby rotate the output shaft 30 in the anti-clockwise direction which causes the hook 44 of the driving lever 40 to move upward. When the output shaft 30 rotates through a predetermined angle the control center will stop the motor 10. At this time, the driving lever 40 is returned to its original position and the hook 44 has pushed the barb 104 upward to thereby withdraw the needle 106 from the patient and return the needle carrier to its retracted position. Alternatively, the motor 10 may drive the worm gear 20 to rotate further in the clockwise direction to return the driving lever 40 to its original position.

In the above embodiment, the worm gear 20, the linkage lever 70, the arm 32 and the output shaft 30 constitutes a four-bar linkage mechanism which forms a rigid transmission device capable of transmitting motion of the motor 10 to the driving lever 40 stably. The encoder disc 80 and the sensor 92 cooperatively form a sensing device which facilitates the control center of the medication delivery device to precisely control rotation of the output shaft 30 to thereby precisely control motion of the driving lever 40. The two projections 39 cooperate with the limit block 68 when the output shaft 30 rotates clockwise and anti-clockwise for ensuring the rotational position of the output shaft 30 is within the predetermined range.

In the description and claims of the present application, each of the verbs "comprise", "include", "contain" and "have", and variations thereof, are used in an inclusive sense, to specify the presence of the stated item but not to exclude the presence of additional items.

Although the invention is described with reference to one or more preferred embodiments, it should be appreciated by those skilled in the art that various modifications are possible. Therefore, the scope of the invention is to be determined by reference to the claims that follow.

The invention claimed is:

1. A lifter assembly for actuating, a needle of an automatic medication delivery device the lifter assembly comprising:
    a motor having a motor shaft;
    a speed reduction device driven by the motor shaft and configured to reduce the rotational speed of the motor shaft;
    an output shaft driven by the weed reduction device via a rigid transmission device:
    a driving lever configured to move the needle the driving lever being connected to and driven by the output shaft; and
    a sensing device configured to sense the rotational position of the output shaft such that a position of the needle is precisely controlled,
    wherein the speed reduction device comprises a worm and a worm gear in mesh with the worm, the rigid transmission device comprising two parts pivotably connected with each other, one of the parts being pivotably connected to a portion of the worm gear offset from the center of the worm gear, the other of the parts being fixed to the output shaft and pivotable about an axis of the output shaft.

2. A lifter assembly for actuating a needle of an automatic medication delivery device, the lifter assembly comprising:
    a motor having a motor shaft;
    a speed reduction device driven by the motor shaft and configured to reduce the speed of the motor shaft, the speed reduction device comprising a worm and a worm gear in mesh with the worm;
    an output shaft driven by the speed reduction device via a rigid transmission device;
    a driving lever configured to move the needle, the driving lever being connected to and driven by the output shaft; and
    a sensing device configured to sense the rotational position of the output shaft;
    wherein the worm gear comprises a connection structure offset from the center of the worm gear,
    wherein the rigid transmission device comprises an arm having one end fixed to the output shaft and the other end extending away from the output shaft, and a linkage lever having two opposite ends respectively pivotably attached to the other end of the arm and to the connection structure of the worm gear, the arm being pivotable about an axis of the output shaft.

3. The lifter assembly of claim 2, wherein the joints between the linkage lever and the worm gear and the arm are formed by a post on one part being pivotably received in a corresponding hole in the other part of the respective joint.

4. The lifter assembly of claim 1, further comprising a housing fastened to the motor, wherein the worm gear, output shaft and rigid transmission device are disposed within the housing.

5. The lifter assembly of claim 1, wherein the lifter assembly further comprises a housing fastened to the motor, and a limit structure is arranged between the housing and the output shaft to prevent the output shaft from rotating beyond a predetermined range.

6. The lifter assembly of claim 5, wherein the limit structure comprises a limit block formed on the housing, and a pair of projections extending from the output shaft and being arranged to abut against the limit block when the output shaft rotates to the end of the predetermined range in a clockwise direction and an anti-clockwise direction, respectively.

7. The lifter assembly of claim 4, wherein the sensing device comprises an encoder disc fixed to and rotatable with the output shaft, and a sensor adjacent to and cooperating with the encoder disc.

8. The lifter assembly of claim 7, further comprising a circuit board fastened to the housing, wherein the sensor is disposed on one side of the circuit board and an electrical connector is disposed on an opposite side of the circuit board and exposed to outside of the housing.

9. The lifter assembly of claim 1, wherein the driving lever is connected to the output shaft via a connecting member which is formed as a monolithic construction with one of the output shaft and the driving lever and is attached to the other of the output shaft and the driving lever.

10. The lifter assembly of claim 1, wherein the driving lever is connected to the output shaft via a connecting member, the connecting member having an end with a non-circular configuration matched with a non-circular hole in the output shaft, an opposite end of the connecting member being fixedly received in a hole in the driving lever.

11. The lifter assembly of claim 1, wherein the worm is fixed to the motor shaft Whereby the motor drives the worm gear via the worm.

12. The lifter assembly of claim 11, wherein the housing comprises a seat, the worm gear is pivotably attached to the seat, the axis of the worm gear is parallel to the axis of the output shaft and perpendicular to the motor shaft.

* * * * *